US006527808B1

(12) United States Patent
Albertorio et al.

(10) Patent No.: US 6,527,808 B1
(45) Date of Patent: Mar. 4, 2003

(54) CONSTRAINED SOCKET FOR USE WITH A BALL-AND-SOCKET JOINT

(75) Inventors: Ricardo Albertorio, Warsaw, IN (US); Robert D. Krebs, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 0 days.

(21) Appl. No.: 09/686,550

(22) Filed: Oct. 11, 2000

(51) Int. Cl.⁷ .................................................. A61F 2/34
(52) U.S. Cl. .................................. 623/22.26; 623/22.24
(58) Field of Search ........................... 623/18.11, 22.26, 623/22.11, 19.12, 21.13, 21.16, 22.15, 22.18, 22.19, 22.21, 22.3, 22.24

(56) References Cited

U.S. PATENT DOCUMENTS

| 3,226,141 A | 12/1965 | Sullivan, Jr. |
| 3,608,096 A | 9/1971 | Link |
| 3,722,002 A | 3/1973 | Charnley |
| 3,863,273 A | 2/1975 | Averill |
| 4,241,463 A | 12/1980 | Khovaylo |
| 4,410,295 A | 10/1983 | Ersoy et al. |
| 4,524,467 A | 6/1985 | DeCarlo, Jr. |
| 4,623,351 A | 11/1986 | Church |
| 4,642,123 A | 2/1987 | Noiles |
| 4,676,798 A | 6/1987 | Noiles |
| 4,678,472 A | 7/1987 | Noiles |
| 4,770,658 A * | 9/1988 | Geremakis ............... 623/22.19 |
| 4,770,659 A * | 9/1988 | Kendall .................... 623/22.19 |
| 4,784,663 A * | 11/1988 | Kenna ....................... 623/22.29 |
| 4,798,610 A | 1/1989 | Averill et al. |
| 4,801,301 A | 1/1989 | Noiles |
| 4,950,299 A | 8/1990 | Noiles |
| 4,960,427 A | 10/1990 | Noiles |
| 4,978,356 A | 12/1990 | Noiles |
| 5,019,105 A * | 5/1991 | Wiley ....................... 623/22.29 |
| 5,387,244 A | 2/1995 | Breard |
| 5,458,649 A | 10/1995 | Spotorno et al. |
| 5,725,591 A | 3/1998 | DeCarlo, Jr. et al. |
| 5,800,555 A | 9/1998 | Gray, III |
| 5,824,108 A | 10/1998 | Huebner |
| 5,916,270 A | 6/1999 | Lipman |

\* cited by examiner

Primary Examiner—David J. Isabella
(74) Attorney, Agent, or Firm—Baker & Daniels

(57) ABSTRACT

An improved constrained socket for use with an orthopedic implant for replacing a ball-and-socket joint. The constrained socket includes cuts extending from the opening of the socket generally toward the articular region thereof. Petals are formed between adjacent cuts in the socket. The socket further includes an annular expansion cutout, with the aforementioned cuts terminating therein. The socket does not include cuts on the primary articular surface, but nevertheless has a relatively low assembly force to allow assembly of the ball-and-socket joint during a surgical procedure. The relatively low assembly force of the constrained socket of the current disclosure is due in part to the annular expansion cutout which allows sufficient outward flexure of the petals to allow insertion of the ball of the ball-and-socket joint. The ball-and-socket joint of the current invention further includes a locking ring with an interior annular beveled surface to facilitate operable positioning of same and with an exterior visual indicator to facilitate identification of the beveled end of the locking ring. The exterior visual indicator comprises an exterior annular protrusion against which axial force may be supplied for positioning the locking ring about the acetabular cup. In one exemplary embodiment, an acetabular liner incorporates the features of the current invention.

26 Claims, 3 Drawing Sheets

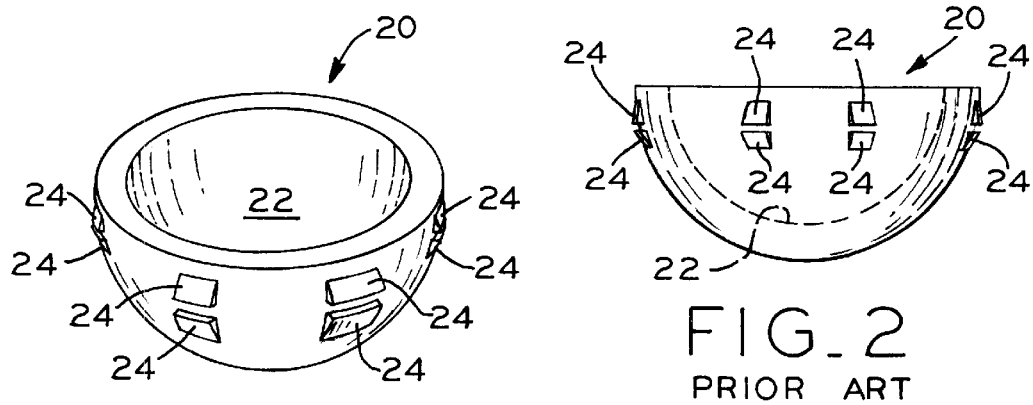
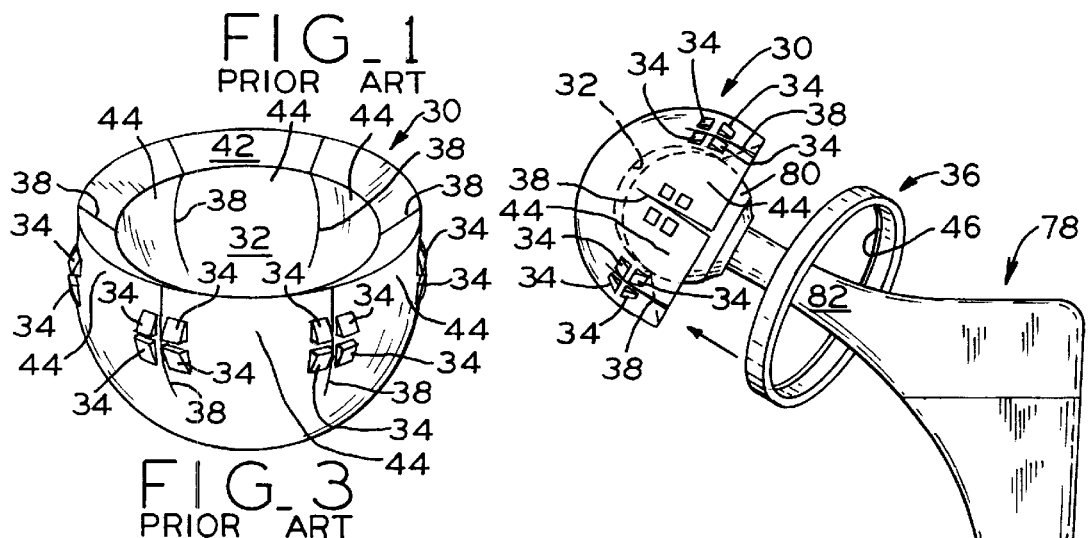
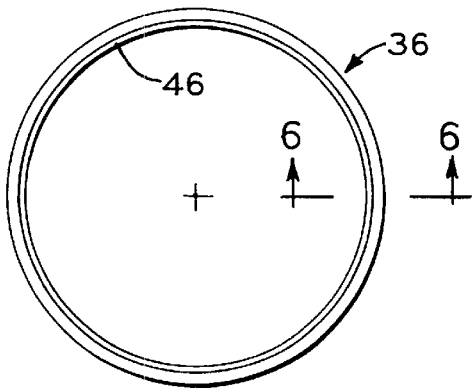
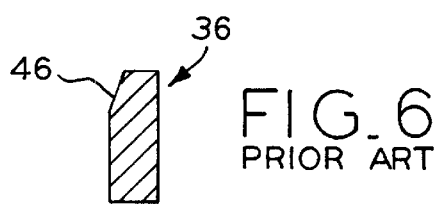
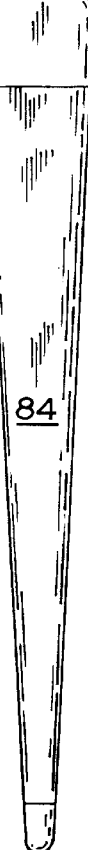

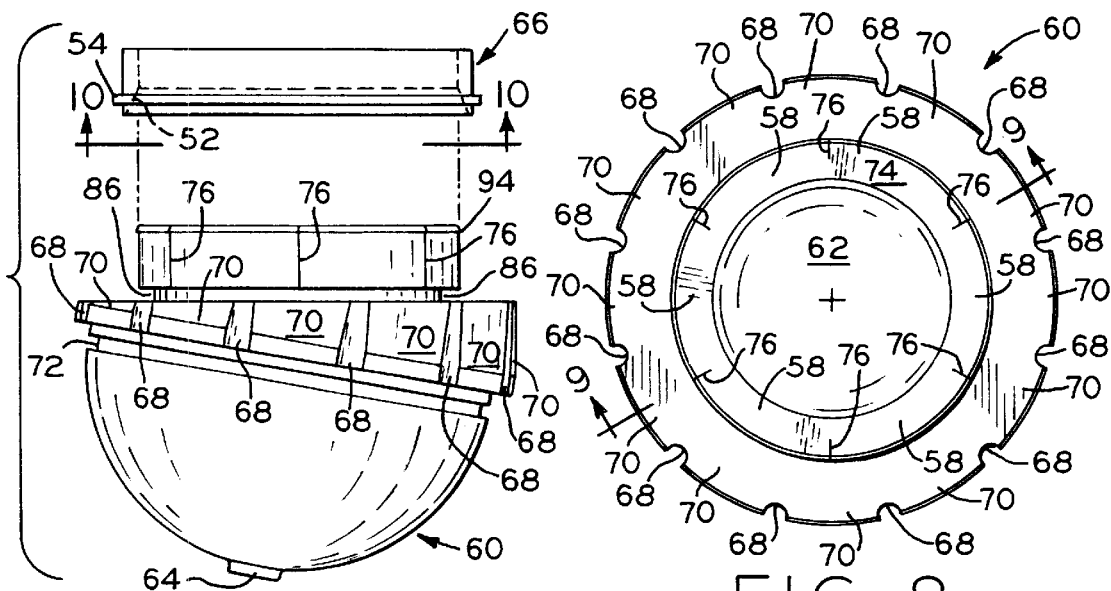
FIG_7
FIG_8
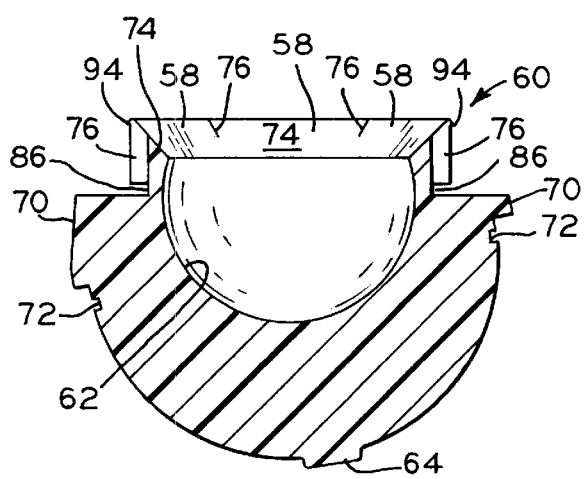
FIG_9
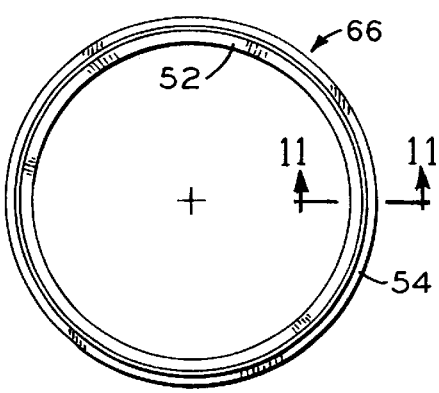
FIG_10
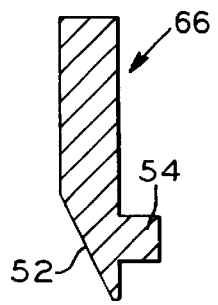
FIG_11
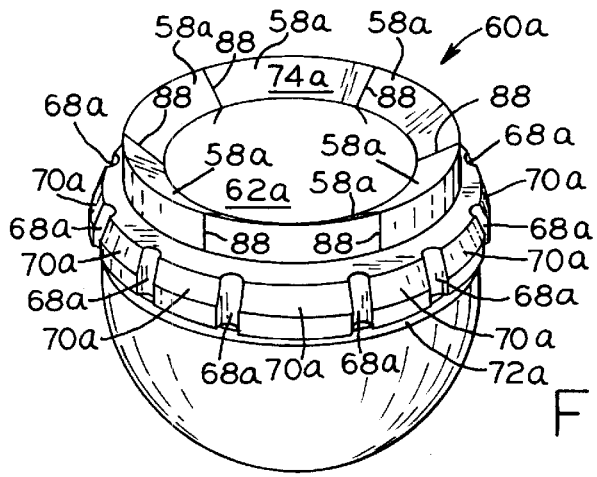
FIG_12

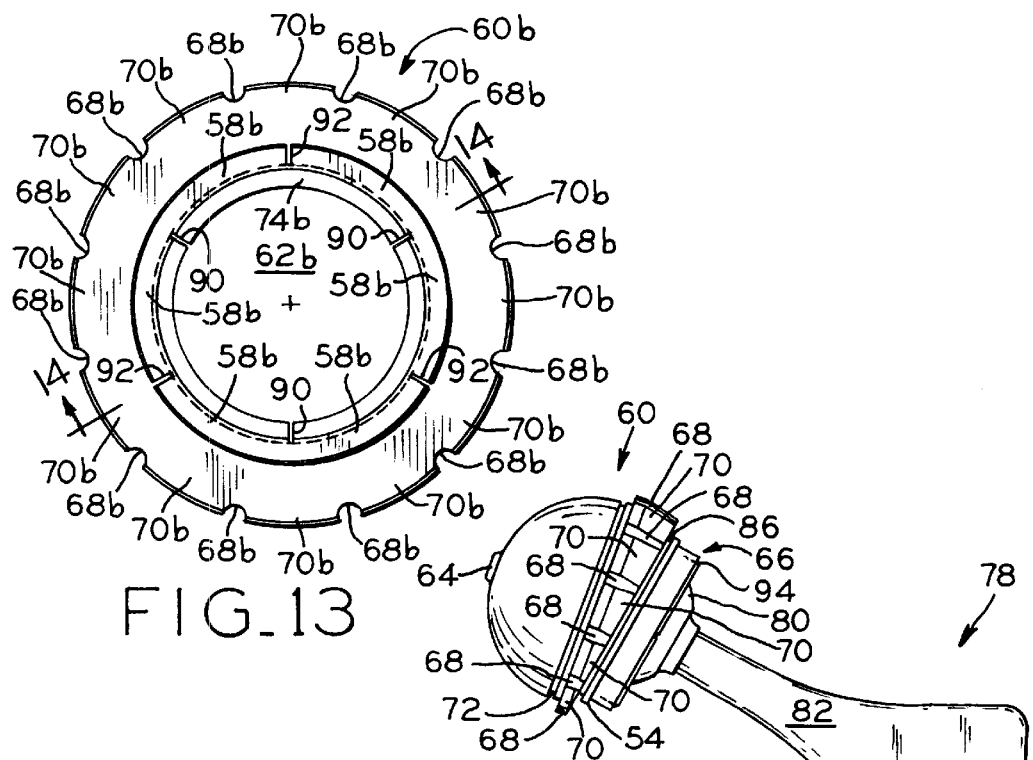
FIG. 13
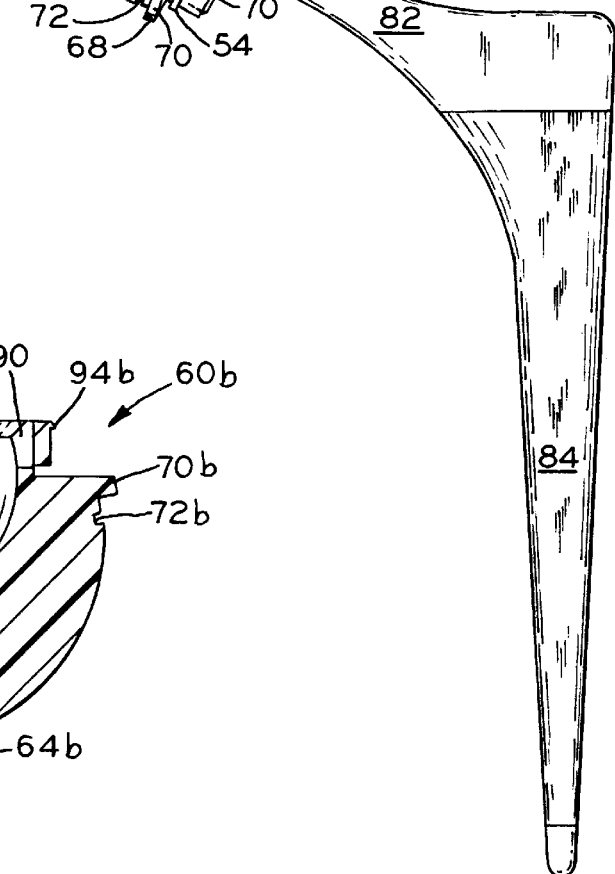
FIG. 14
FIG. 15

CONSTRAINED SOCKET FOR USE WITH A BALL-AND-SOCKET JOINT

BACKGROUND OF THE INVENTION

1. Field of the Invention

The present invention relates to ball-and-socket joints, and, more particularly, to an improved liner forming the socket of an orthopaedic implant utilized to replace (in whole, or in part) a ball-and-socket joint.

2. Description of the Related Art

Orthopaedic implants for the replacement of all, or a portion of, a patient's joint such as, e.g., the ball-and-socket joints of, e.g., the shoulder and hip are commonly used to restore the use of, or increase the use of a joint which has deteriorated due to, e.g., aging, illness, or injury. For the sake of brevity, this document will describe a ball-and-socket joint with reference to the hip joint, however, it will be understood that the disclosure of this document is adaptable to any ball-and-socket joint, including, e.g., the shoulder joint.

Typically, orthopaedic implants for replacing a patient's hip include a femoral component and an acetabular component. The femoral component includes the "ball" of the joint, while the acetabular component includes the "socket". The femoral component is designed to replace the head and the neck of the femur, while the acetabular component is positioned in the acetabulum and includes an articular region to receive the head of the femoral component and to allow relative movement between the femoral component and the acetabular component. The head of the femoral component is generally spherical, and the articular region of the acetabular component includes a corresponding spherical cavity to accommodate the head of the femoral component and form the desired ball-and-socket joint.

The acetabular component typically includes both a cup and a liner, with the cup being formed from, e.g., stainless steel or titanium and the liner being formed from ultra-high molecular weight polyethylene (UHMWPE). It is further known that the liner can be formed from a plastic other than UHMWPE and can also be formed from metal. The current disclosure is adaptable to the various materials of construction of the acetabular component.

In a known prosthetic hip joint, the liner of the acetabular component forms the articular region thereof. The acetabular cup is affixed to the acetabulum and the liner is thereafter affixed to the shell and receives the femoral head. Known procedures for affixation of the acetabular cup include, e.g., the use of screws to traverse apertures in the acetabular cup, be sunk into the acetabulum, and thereby effect affixation of the acetabular cup to the acetabulum. The liner of the acetabular component typically includes exterior protrusions and/or indentations which mate with indentations and/or protrusions on the interior of the shell to effect affixation of the liner to the shell and form the complete acetabular component.

The acetabular component described above includes a single articulating surface, however, it is known to provide an acetabular component which is not affixed to, but rather is movable within the natural socket of the acetabulum and therefore includes a pair of articulating surfaces (i.e., the head of the femoral component is moveable against the articular region of the acetabular component and also the acetabular component is moveable within the natural socket of the acetabulum). These devices having a pair of articulating surfaces are generally referred to as "bipolar". The constrained acetabular liner of the current invention is applicable to both of the above-described types of acetabular components.

In one known prior art hip implant, the articular region of the acetabular component is hemispherical, and, therefore, the head of the femoral component is not "constrained" or held in place by the acetabular component. In such arrangements, the muscles, tendons and ligaments of the individual receiving the implant function to hold the femoral component in place within the articular region of the acetabular component. FIGS. 1 and 2 illustrate prior art acetabular liner 20 including hemispherical articular region 22. Acetabular liner 20 further includes affixing protrusions 24 to affix acetabular liner 20 to an acetabular cup to form the complete acetabular component, as described above. Since articular region 22 will not hold the head of a femoral component in place, acetabular liners of this type may result in a relatively high incidence of hip dislocation.

Alternatives to hemispherical acetabular liners include so-called "constrained" acetabular liners. Constrained acetabular liners are characterized in that the head of the femoral component is physically restrained by the acetabular liner after being positioned in abutting relationship with the articular region of the acetabular liner. Constrained acetabular liners have a spherical articular region and are generally spherically shaped themselves. The articular region of a constrained acetabular liner is formed in a cavity of the acetabular liner which is larger than a hemisphere, so that the acetabular liner surrounds more than a hemisphere of the femoral head and, therefore, constrains the femoral head from dislocation from the acetabular component.

While constrained acetabular components advantageously decrease the frequency of joint dislocation, they present assembly problems for the surgeons who implant them. Generally, the more constrained (i.e., the more material of the acetabular liner extending beyond a hemisphere) an acetabular component is, the more difficult the ball-and-socket joint is to assemble. With this in mind, many constrained ball-and-socket joints have an assembly force which necessitates assembly of the femoral head into the articular region of the acetabular component prior to implantation (i.e., not during the surgical procedure). This assembly procedure limits the versatility of these components and, specifically, limits a surgeon's ability to choose an alternative prosthesis during a surgical procedure.

With the above problems in mind, constrained acetabular components having an assembly force which is disproportionately lower when compared to the dislocation force of the assembled prosthesis have been developed. FIGS. 3 and 4 illustrate prior art acetabular liner 30 having spaced cuts 38 extending from beveled rim 42 into articular region 32. Acetabular liner 30 further includes affixing protrusions 34 analogous to affixing protrusions 24 described above with respect to acetabular liner 20 illustrated in FIGS. 1 and 2.

Prior art acetabular liner 30 includes petals 44 formed between adjacent cuts 38. FIG. 4 illustrates insertion of femoral component 78 into acetabular liner 30. As illustrated in FIG. 4, petals 44 flex outwardly as femoral head 80 is inserted into acetabular liner 30. FIG. 4 illustrates femoral head 80 prior to being fully seated against articular region 32. As illustrated, in this transitional state, cuts 38 separate to allow petals 44 to flex outwardly, thus increasing the size of the opening in acetabular liner 30 and decreasing the required assembly force to operatively position femoral head 80 in abutting relationship with articular region 32.

Referring to FIG. 3, acetabular liner 30 includes beveled rim 42 adjacent the opening to facilitate positioning and insertion of femoral head 80. After femoral head 80 is fully seated within acetabular liner 30, locking ring 36 will be positioned generally about the exterior portion of acetabular liner 30 surrounding beveled rim 42. When operably positioned about acetabular liner 30, locking ring 36 prevents outward flexure of petals 44, thus increasing the dislocation force required to remove femoral head 80 from acetabular liner 30.

FIGS. 5 and 6 more fully illustrate prior art locking ring 36. As illustrated, locking ring 36 includes beveled annular surface 46 to facilitate placement of locking ring 36 about acetabular liner 30. As illustrated in FIG. 4, locking ring 36 is placed about femoral neck 82 prior to being operably positioned about acetabular liner 30. Locking ring 36 utilized with this prior art prosthesis may be incorrectly positioned about femoral neck 82 (i.e., with beveled annular surface 46 being positioned on the end of locking ring 36 facing femoral stem 84, as opposed to the end of locking ring 36 facing femoral head 80) since no external indicator of the beveled surface is provided. When such mis-positioning occurs, beveled annular surface 46 is ineffective in facilitating the placement of locking ring 36 about acetabular liner 30. Furthermore, acetabular liner 30 includes a locking lip (not shown) for retaining locking ring 36 in operable position about acetabular liner 30, therefore, if locking ring 36 is mis-positioned, the locking lip will be positioned adjacent beveled annular surface 46, and, consequently, locking ring 36 will be susceptible to axial displacement and may be more easily removed from acetabular liner 30. Also, locking ring 36 can be difficult to position about acetabular liner 30, as the surgeon's hand may slip over locking ring 36 as axial force is supplied to locking ring 36.

What is needed in the art is a constrained socket, and, specifically, a constrained acetabular liner which does not include cuts extending into the articular region.

What is further needed in the art is a locking ring for use with a constrained socket, and, specifically, a constrained acetabular component, which locking ring is structured to facilitate operative positioning thereof by a surgeon.

SUMMARY OF THE INVENTION

The present invention provides an improved constrained socket for use in an orthopaedic implant for replacing a ball-and-socket joint. In one form of the current invention, the improved socket construction is embodied in an improved constrained acetabular liner. The constrained socket of the current invention includes cuts extending from the opening of the socket generally toward, but not into, the primary articular region. For the purposes of this document, the "primary articular region" or "primary articular surface" refers to the portion of the cavity in the socket of a ball-and-socket joint in the lower hemisphere of the cavity, with the lower hemisphere defined as the portion below an equatorial line residing in a plane which is substantially perpendicular to a plane containing the rim of the socket surrounding its opening. The socket further includes an annular expansion cutout, with the aforementioned cuts terminating therein. A plurality of petals are formed between adjacent cuts and are operable to flex outwardly to facilitate operable positioning of a ball within the socket.

The constrained socket of the current invention is absent cuts on the primary articular surface, but nevertheless has a relatively low assembly force. This is due in part to the annular expansion cutout which allows sufficient outward flexure of the petals to allow insertion of the ball of a prosthetic ball-and-socket joint. The ball-and-socket joint of the current invention further includes a locking ring with an interior annular beveled surface to facilitate operable positioning of same and with an exterior visual indicator to facilitate identification of the beveled end of the locking ring. The exterior visual indicator of the locking ring of the current invention comprises an annular exterior protrusion against which axial force may be supplied to facilitate positioning the locking ring and decrease the problem associated with a surgeon's hand slipping along the locking ring.

The invention, in one form thereof, comprises an implantable prosthetic ball-and-socket joint. The ball-and-socket joint of this form of the current invention includes a ball connected to a component adapted for affixation to an articulating bone as well as a socket having a generally spherical cavity and an opening for receiving the ball. The socket of this form of the current invention is adapted for affixation to a bony structure, and the cavity includes an articular region for abutting the ball when it is operably positioned therein. The socket further includes at least one partial exterior cut extending through the exterior of the socket, but not into the cavity. The cut allows a portion of the socket near the opening of the socket to flex outwardly to allow the ball to traverse the opening and be positioned in abutting relationship with the articular region.

The invention, in another form thereof, comprises an implantable prosthetic ball-and-socket joint. The ball-and-socket joint of this form of the current invention includes a ball connected to a component adapted for affixation to an articulating bone as well as a socket having a generally spherical cavity and an opening for receiving the ball. The socket of this form of the current invention is adapted for affixation to a bony structure, and the cavity includes a primary articular region for abutting the ball when it is operably positioned therein. The socket further includes at least one cut extending generally from the opening of the socket toward, but not into, the primary articular region of the socket. The cut allows a portion of the socket near the opening to flex outwardly to allow the ball to traverse the opening of the socket and be positioned in abutting relationship with the primary articular region.

The invention, in a further form thereof, comprises an implantable prosthetic ball-and-socket joint. The ball-and-socket joint of this form of the current invention includes a ball connected to a component adapted for affixation to an articulating bone and a socket. The socket includes a generally spherical cavity as well as an opening for receiving the ball of the joint. The socket is adapted for affixation to a bony structure and the cavity includes an articular region for abutting the ball of the joint. The socket further includes an annular expansion cutout for allowing a portion of the socket near the opening of the socket to flex outwardly to allow the ball of the joint to traverse the opening in the socket and be positioned in abutting relationship with the primary articular region.

The invention, in yet another form thereof, comprises an implantable prosthetic ball-and-socket joint. The ball-and-socket joint of this form of the current invention includes a ball connected to a component adapted for affixation to an articulating bone as well as a socket having a generally spherical cavity and an opening for receiving the ball. The socket is adapted for affixation to a bony structure, with the cavity therein including a primary articular region for abutting the ball. The socket includes at least one cut extending generally from the opening toward the primary articular region to allow a portion of the socket near the opening to flex outwardly to allow the ball to traverse the opening and be positioned in abutting relationship with the primary articular region. The implantable prosthetic of this form of the current invention further includes a locking ring for surrounding the opening of the socket and preventing flexure of the portion of the socket near the opening. The locking ring includes an interior annular beveled surface located at a first end of the locking ring, and further includes an exterior annular protrusion operable to identify the first end of the locking ring.

An advantage of the present invention is the ability to provide a constrained socket for a ball-and-socket joint which facilitates placement of the ball in the socket, but which does not include cuts extending into any portion of the articular region.

Another advantage of the present invention is the ability to provide a constrained socket for a ball-and-socket joint which facilitates placement of the ball in the socket, but which does not include cuts extending into the primary articular region.

Another advantage of the present invention is the provision of a locking ring having an external identifier to facilitate proper positioning thereof.

A further advantage of the present invention is the provision of a locking ring including a radially extending member against which axial force may be supplied to facilitate operable positioning of the locking ring.

BRIEF DESCRIPTION OF THE DRAWINGS

The above mentioned and other features and objects of this invention, and the manner of attaining them, will become more apparent and the invention itself will be better understood by reference to the following description of embodiment of the invention taken in conjunction with the accompanying drawings, wherein:

FIG. 1 is a perspective view of a prior art acetabular liner;

FIG. 2 is a side elevational view thereof;

FIG. 3 is a perspective view of a constrained acetabular liner of the prior art;

FIG. 4 is an elevational view illustrating positioning of a femoral component into the constrained acetabular liner illustrated in FIG. 3;

FIG. 5 is an axial elevational view of a prior art retaining ring;

FIG. 6 is a sectional view thereof;

FIG. 7 is an exploded, side elevational view of an acetabular liner and locking ring in accordance with the present invention;

FIG. 8 is a top elevational view of the acetabular liner illustrated in FIG. 7;

FIG. 9 is a sectional view thereof;

FIG. 10 is an axial elevational view of a locking ring in accordance with the present invention;

FIG. 11 is a sectional view thereof;

FIG. 12 is a perspective view of an alternative embodiment of an acetabular liner in accordance with the present invention;

FIG. 13 is a top elevational view of a further embodiment of an acetabular liner in accordance with the present invention;

FIG. 14 is a sectional view thereof; and

FIG. 15 is an elevational view of an acetabular liner in accordance with the present invention operably connected to a femoral component.

Corresponding reference characters indicate corresponding parts throughout the several views. Although the drawings represent embodiments of the present invention, the drawings are not necessarily to scale and certain features may be exaggerated to better illustrate and explain the invention. The exemplification set out herein illustrates exemplary embodiments of the invention only and such exemplifications are not to be construed as limiting the scope of the invention in any manner.

DETAILED DESCRIPTION OF THE INVENTION

The following detailed description refers to acetabular liners incorporating the features of the current invention. While this description refers to acetabular liners, the teachings of the current invention are applicable to any constrained socket forming a part of a ball-and-socket joint. Referring now to the drawings and particularly to FIG. 7, there is illustrated acetabular liner 60 including cuts 76. As illustrated in FIG. 8, cuts 76 are partial exterior cuts which do not extend into articular region 62. It will be appreciated that any cut which does not extend into articular region 62 will also not extend into the primary articular region. Partial exterior cuts 76 are further illustrated in FIG. 9. As illustrated in FIG. 9, partial exterior cuts 76 extend from beveled rim 74 and terminate at annular expansion cutout 86. Partial exterior cuts 76 separate beveled rim 74 into a plurality of petals 58. Acetabular liner 60 further includes anti-rotation indentations 68 and anti-rotation tabs 70 as well as placement boss 64 and annular placement groove 72 for affixing acetabular liner 60 to an acetabular cup as is known in the art.

FIG. 15 illustrates acetabular liner 60 operatively positioned about femoral head 80 of femoral component 78. As is known in the art, femoral component 78 further includes femoral neck 82 and femoral stem 84 and is designed for affixation to a femur. Petals 58 (FIGS. 8 and 9) of acetabular liner 60 allow for insertion of femoral head 80 into acetabular liner 60. As femoral head 80 is inserted into acetabular liner 60, petals 58 are flexed outwardly to increase the size of the opening of the acetabular liner, thus allowing femoral head 80 to traverse the opening, and be positioned in abutting relationship with articular region 62 (FIG. 9).

Petals 58 have sufficient flexure to permit femoral head 80 to traverse the opening of acetabular liner 60 even though cuts 76 are only partial cuts (i.e., they do not extend into the interior of acetabular liner 60) which do not extend into articular region 62. This is due to the placement of annular expansion cutout 86. Annular expansion cutout 86 allows for sufficient outward flexure of petals 58 to accommodate insertion of femoral head 80. It is important here to note that femoral head 80 is sized so that it will abut articular region 62 of acetabular liner 60 when operably positioned therein. With this in mind, it is clear that since the interior cavity of acetabular liner 60 extends further than a hemisphere, the opening of acetabular liner 60 will not be large enough to accommodate femoral head 80, thus necessitating flexure of petals 58. Once femoral head 80 is operably positioned within acetabular liner 60, locking ring 66 is positioned about the periphery of the portion of acetabular liner 60 extending upwardly from annular expansion cutout 86 and terminating at locking protrusion 94, which will be discussed further herein below.

FIG. 15 illustrates locking ring 66 operably positioned about acetabular liner 60, while FIG. 7 illustrates alignment of locking ring 66 prior to positioning about acetabular liner 60. Locking ring 66 includes interior annular beveled surface 52 and exterior annular protrusion 54 as illustrated, e.g., in FIGS. 10 and 11. As illustrated in FIG. 11, interior annular beveled surface 52 and exterior annular protrusion 54 are positioned toward the same end of locking ring 66. Exterior annular protrusion 54 serves multiple functions (1) it identifies the end of locking ring 66 having interior annular beveled surface 52, (2) it facilitates operable positioning of locking ring 66, as axial force can be applied to exterior annular protrusion 54, (3) it provides a surface against which an instrument can be positioned to supply axial force and remove locking ring 66 from placement about acetabular liner 60, and (4) it increases the strength of locking ring 66. Thus, exterior annular protrusion 54 substantially eliminates the problems associated with identification of the interior annular beveled surface and with the surgeon's hand slipping along the exterior surface of locking ring 66. When operably positioned about acetabular liner 60 as illustrated in FIG. 15, locking ring 66 prevents outward flexure of petals 58 thus retaining femoral head 80 within acetabular liner 60. Once locking ring 66 is operably positioned about acetabular liner 60, locking protrusion 94 retains locking ring 66 and prevents accidental removal thereof. In one exemplary embodiment, locking ring 66 is formed from TIVANIUM.

FIGS. 12, 13, and 14 illustrate alternative embodiments of an acetabular liner in accordance with the present invention. Referring now to FIG. 12, acetabular liner 60a includes beveled rim 74, anti-rotation indentation 68a, anti-rotation tabs 70a and annular placement groove 72a similar to acetabular liner 60 discussed above. Acetabular liner 60a further includes articular region 62a against which femoral head 80 will be placed. Acetabular liner 60a differs from acetabular liner 60 in that cuts 88 are full cuts which are made through the entire thickness of acetabular liner 60a. However, cuts 88 do not extend into the primary articular region of acetabular liner 60a. While acetabular liner 60a does not include an annular expansion cutout as described above with respect to acetabular liner 60, such an annular expansion cutout could be added to acetabular liner 60a. Without annular expansion cutout 86, flexure of petals 58a will be limited relative to flexure of petals 58 of acetabular liner 60 described above, however, such a construction will provide an acceptable insertion force depending upon the thickness of acetabular liner 60a in the area through which cuts 88 are made. The adequacy of acetabular liner 60a will, of course, be a function of the level of constrainment (i.e., the amount of acetabular liner 60a extending beyond a hemisphere) provided by acetabular liner 60a.

FIGS. 13 and 14 illustrate acetabular liner 60b. Acetabular liner 60b is substantially similar to acetabular liner 60 and includes beveled rim 74b, articular region 62b, anti-rotation indentation 68b, anti-rotation tabs 70b, placement boss 64b, and annular placement groove 72b. Acetabular liner 60b includes exterior partial cuts 92 as well as interior partial cuts 90, forming petals 58b therebetween. Acetabular liner 60b further includes annular expansion cutout 86b which allows for greater outward flexure of petals 58b. As illustrated in FIG. 14, beveled rim 74a does not intersect exterior partial cuts 92. Since beveled rim 74a does not intersect exterior partial cuts 92, no portion of exterior partial cuts 92 will be visible from the interior of acetabular liner 60b. Depending upon the required flexure of petals 58b, differing combinations of interior partial cuts 90 and exterior partial cuts 92 may be utilized.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An implantable prosthetic ball-and-socket joint comprising:
    a ball connected to a component adapted for affixation to an articulating bone;
    a socket having an exterior wall and an interior wall, said interior wall defining a generally spherically cavity, said socket having an opening for receiving said ball, said socket adapted for affixation to a bony structure, said cavity including an articular region for abutting said ball, said socket including at least one partial exterior cut extending through said exterior wall of said socket, wherein said cut does not extend into said cavity, said cut allowing a portion of said socket near said opening to flex outwardly to allow said ball to traverse said opening and be positioned in abutting relationship with said articular region.

2. The implantable prosthetic ball-and-socket joint according to claim 1, further comprising an annular expansion cutout formed in said exterior wall, wherein said annular expansion cutout facilitates flexure of said portion of said socket near said opening to allow said ball to traverse said opening and be positioned in abutting relationship with said articular region.

3. The implantable prosthetic ball-and-socket joint according to claim 2, wherein said cut terminates in said annular expansion cutout.

4. The implantable prosthetic ball-and-socket joint according to claim 1, further comprising a locking ring for engaging said exterior wall of said socket and thereby preventing flexure of said portion of said socket near said opening.

5. The implantable prosthetic ball-and-socket joint according to claim 4, wherein said locking ring includes an interior annular beveled surface located at a first end of said locking ring, and wherein said locking ring further includes an exterior annular protrusion operable to identify said first end of said locking ring.

6. The implantable prosthetic ball-and-socket joint according to claim 1, further comprising an annular expansion cutout formed in said exterior wall, wherein said annular expansion cutout facilitates flexure of said portion of said socket near said opening to allow said ball to traverse said opening and be positioned in abutting relationship with said primary articular region.

7. The implantable prosthetic ball-and-socket joint according to claim 6, wherein said cut terminates in said annular expansion cutout.

8. The implantable prosthetic ball-and-socket joint according to claim 1, wherein said component is a femoral component adapted for affixation to a femur.

9. The implantable prosthetic ball-and-socket joint according to claim 1, wherein said interior wall includes a beveled rim adjacent said opening.

10. An implantable prosthetic ball-and-socket joint comprising:
    a ball connected to a component adapted for affixation to an articulating bone; and
    a socket having an exterior wall and an interior wall, said interior wall defining a generally spherical cavity, said socket having an opening for receiving said ball, said socket adapted for affixation to a bony structure, said cavity including a primary articular region for abutting said ball, said socket including at least one partial exterior cut extending through said exterior wall of said socket, wherein said cut does not extend into said cavity, said cut allowing a portion of said socket near said opening to flex outwardly to allow said ball to traverse said opening and be positioned in abutting relationship with said primary articular region.

11. An implantable prosthetic ball-and-socket joint comprising:
   a ball connected to a component adapted for affixation to an articulating bone; and
   a socket having an exterior wall and an interior wall, said interior wall defining a generally spherical cavity, said socket having an opening for receiving said ball, said socket adapted for affixation to a bony structure, said cavity including a primary articular region for abutting said ball, said socket including at least one partial interior cut extending through said interior wall of said socket, but not into said primary articular region, said cut allowing a portion of said socket near said opening to flex outwardly to allow said ball to traverse said opening and be positioned in abutting relationship with said primary articular region.

12. An implantable prosthetic ball-and-socket joint comprising:
   a ball connected to a component adapted for affixation to an articulating bone; and
   a socket having an exterior wall and an interior wall, said interior wall defining a generally spherical cavity, said socket having an opening for receiving said ball, said socket adapted for affixation to a bony structure, said cavity including a primary articular region for abutting said ball, said socket including at least one partial interior cut extending through said interior wall of said socket, but not into said primary articular region said socket further including at least one partial exterior cut extending through said exterior wall of the socket, but not into said primary articular region, said cut allowing a portion of said socket near said opening to flex outwardly to allow said ball to traverse said opening and be positioned in abutting relationship with said primary articular region.

13. The implantable prosthetic ball-and-socket joint according to claim 10, further comprising a locking ring engaging said exterior wall of said socket and thereby preventing flexure of said portion of said socket near said opening.

14. The implantable prosthetic ball-and-socket joint according to claim 13, wherein said locking ring includes an interior annular beveled surface located at a first end of said locking ring, and wherein said locking ring further includes an exterior annular protrusion operable to identify said first end of said locking ring.

15. The implantable prosthetic ball-and-socket joint according to claim 13, wherein said locking ring is formed from a titanium alloy.

16. The implantable prosthetic ball-and-socket joint according to claim 13, wherein said exterior wall of said socket includes an annular lock protrusion for locking said locking ring in place about said opening.

17. The implantable prosthetic ball-and-socket joint according to claim 10, wherein said socket includes a plurality of retaining elements for preventing movement of said socket in said bony structure.

18. The implantable prosthetic ball-and-socket joint according to claim 10, further comprising:
   a placement boss extending from said exterior wall of said socket;
   a plurality of anti-rotation indentations formed in said exterior wall of said socket;
   a plurality of anti-rotation tabs extending from said exterior wall of said socket; and
   an annular placement groove formed in said exterior wall of said socket.

19. The implantable prosthetic ball-and-socket joint according to claim 10, wherein said socket is formed from ultra-high molecular weight polyethylene.

20. An implantable prosthetic ball-and-socket joint comprising:
   a ball connected to a component adapted for affixation to an articulating bone; and
   a socket including;
      an exterior wall;
      an interior wall, said interior wall defining a generally spherical cavity;
      an opening for receiving said ball, said socket adapted for affixation to
   a bony structure, said cavity including an articular region for abutting said ball; and
      an annular expansion cutout, said annular expansion cutout allowing a portion of said socket near said opening to flex outwardly to allow said ball to traverse said opening and be positioned in abutting relationship with said articular region, wherein said socket includes a partial exterior cut extending through said exterior wall of said socket, wherein said cut does not extend into said cavity.

21. The implantable prosthetic ball-and-socket joint according to claim 20, wherein said component is a femoral component adapted for affixation to a femur.

22. The implantable prosthetic ball-and-socket joint according to claim 20, wherein said socket is formed from ultra-high molecular weight polyethylene.

23. The implantable prosthetic ball-and-socket joint according to claim 20, further comprising a locking ring for engaging said exterior wall of said socket and thereby preventing flexure of said portion of said socket near said opening.

24. The implantable prostetic ball-and-socket joint according to claim 23, wherein said locking ring includes an interior annular beveled surface located at a first end of said locking ring, and wherein said locking ring further includes an exterior annular protrusion operable to identify said first end of said locking ring.

25. An implantable prosthetic ball-and-socket joint comprising:
   a ball connected to a component adapted for affixation to an articulating bone;
   a socket having an exterior wall and an interior wall, said interior wall defining generally spherical cavity, said socket having an opening for receiving said ball, said socket adapted for affixation to bony structure, said cavity including an articular region for abutting said ball, said socket including at least one cut extending generally from said opening toward said articular region, said cut allowing a portion of said socket near said opening to flex outwardly to allow said ball to traverse said opening and be positioned in abutting relationship with said articular region; and
   a locking ring for engaging said exterior wall of said socket and thereby preventing flexure of said portion of said socket near said opening, said locking ring including an interior annular beveled surface located at a first end of said locking ring, and wherein said locking ring further includes an exterior annular protrusion operable to identify said first end of said locking ring, said locking ring formed from a titanium alloy.

26. The implantable prosthetic ball-and-socket joint according to claim 25, wherein said exterior wall of said socket includes an annular lock protrusion for locking said locking ring in place about said opening.

* * * * *